United States Patent [19]
Allemand

[11] Patent Number: 4,655,592
[45] Date of Patent: Apr. 7, 1987

[54] PARTICLE DETECTION METHOD AND APPARATUS

[75] Inventor: Charly D. Allemand, Newtonville, Mass.

[73] Assignee: Hamamatsu Systems, Inc., Waltham, Mass.

[21] Appl. No.: 567,407

[22] Filed: Dec. 30, 1983

[51] Int. Cl.$^4$ ............................................. G01N 21/47
[52] U.S. Cl. ...................... 356/237; 219/121 LQ; 350/620; 350/622; 350/625; 356/338; 362/297; 250/222.2; 250/572
[58] Field of Search ............................. 250/572, 222.2; 356/340, 337, 221, 446, 338, 38, 335, 336, 237; 362/297, 346, 347; 350/168, 525, 619, 620, 622, 625; 219/121 LQ

[56] References Cited

U.S. PATENT DOCUMENTS

| | | | |
|---|---|---|---|
| 2,097,494 | 11/1937 | Lihotzky | 350/525 |
| 2,930,287 | 3/1960 | Franks | 350/619 |
| 3,782,836 | 1/1974 | Fey et al. | 356/446 |
| 3,930,713 | 1/1976 | Stankewitz et al. | 350/525 |
| 4,127,318 | 11/1978 | Determann et al. | 350/525 |
| 4,377,340 | 3/1983 | Green et al. | 356/237 |
| 4,449,818 | 5/1984 | Yamaguchi et al. | 250/572 |

FOREIGN PATENT DOCUMENTS

| | | | |
|---|---|---|---|
| 0608644 | 1/1935 | Fed. Rep. of Germany | 350/525 |
| 0401591 | 11/1933 | United Kingdom | 350/525 |

OTHER PUBLICATIONS

IBM Tech. Disclosure Bull., vol. 22, #4, p. 1360, Aug. 1979.
IBM T.D.B., vol. 2, #10, p. 1672, Mar. 1970.
IBM T.D.B., vol. 21, #6, p. 2336, Nov. 1978.

*Primary Examiner*—John E. Kittle
*Attorney, Agent, or Firm*—Irving M. Kriegsman

[57] ABSTRACT

An apparatus and method are disclosed for detecting the presence of particles on the surface of a material, such as a semiconductor wafer, using the principle of scattered light. Light from a mercury arc lamp is collimated by a Cassegrain mirror collimator. The collimated beam of light is deflected by an annular shaped 45° mirror toward a truncated annular shaped inverted parabolic mirror. Light striking the parabolic mirror is reflected outward in all directions as a converging beam of light toward a ring mirror. Light striking the ring mirror is reflected inward and strikes the surface from all directions at an angle of about 78° to 86° from normal incidence as a small spot. An objective lens located a distance directly above the area on the surface illuminated by the spot of light and mounted at one end of a light tight tube collects light scattered by any particles on the surface, but not light reflected by the surface, and forms an image of the light so collected on the light sensitive surface of a photodetector mounted at the other end of the tube. The wafer is mounted on a holder which is movable rotationally and translationally relative to the impinging light beam so that the entire surface of the wafer may be scanned by the light beam, an area at a time.

18 Claims, 4 Drawing Figures

PARTICLE DETECTION METHOD AND APPARATUS

BACKGROUND OF THE INVENTION

The present invention relates generally to a method and apparatus for detecting the presence of particles on a material and more particularly to a method and apparatus for detecting the presence of particles on a material using the scattered light principle.

Although the invention is especially useful in detecting particles on a material such as the surface of a semiconductor wafer, it is to be understood that the invention is applicable for use in connection with other materials, objects or bodies.

In the prior art there are a variety of ways in which to detect and measure the number and sizes of particles on a semiconductor wafer, for the purpose of rejecting those wafers which have on their surface one or more particles above certain sizes, e.g. from 1 to 20 microns, or for those having on their surface an excessive number of particles.

One of the most prevalent methods employs the human operator using a light field/dark field microscope. Using the eye, the operator actually counts the number of particles and also identifies the size of the particles, such as those between 1 to 20 microns, and then rejects those wafers which have an excessive number of particles or those having particles of or above a certain size. This method is without doubt highly inaccurate, and very expensive both in terms of wages for the human operator, and in terms of the number of rejects both after the inspection and after production of the chips (when an erroneously passed wafer is found to have an electrical defect, e.g. short circuits, because of the presence of contaminant particles).

In U.S. Pat. No. 4,377,340 to G. P. Green etc., there is disclosed a method and apparatus for detecting and measuring the number and sizes of impurities on the surface of a material, such as a semiconductor wafer, wherein a beam of high intensity collimated light is directed onto the surface at normal incidence in the absence of any extraneous light, through a collimating mirror and employing a point source, whereat the particles will scatter the light, and wherein the surface is viewed by a highly light sensitive TV camera which picks up scattered light only and displays the scattered light on a viewing screen.

In IBM Technical Disclosure Bulletin Volume 2, No. 10, pages 1672–1673, dated March, 1970, there is disclosed a system for detecting repeated geometric defects on a reflecting surface in which a collimated light beam strikes the surface being examined at a finite angle of incidence. Light scattered back along the same axis as the angle of incidence is directed through a telescope to a photomultiplier tube.

In IBM Technical Disclosure Bulletin Volume 21, No. 6, pages 2336–2337 dated November, 1978, there is disclosed a system for detecting defects on wafers wherein light from a plurality of ring light sources impinges on the wafer at an oblique angle to the wafer surface and wherein light scattered upward from the surface at right angles thereto is fed by a lens system into a broad band array detector.

An attachment has been reported for use with a microscope of the type having a 45° mirror mounted on the microscope tube and a lateral opening along the length of the microscope tube to enable the entire mirror surface to receive a collimated beam of light directed to the mirror from a source next to the microscope tube. The attachment is a single optical element made of glass which is mounted on the tube in axial alignment therewith. The optical element contains a first curved reflective surface for causing the light reflected from the 45° mirror to be made converging and sent out in all directions and a second curved reflective surface for redirecting the converging light beam so that it comes to focus underneath the microscope tube from all directions. As can be appreciated, any imperfections or bubbles in the glass will produce scattering as the light beam passes from the first reflective surface through the optical element to the second reflective surface.

It is an object of this invention to provide a new and improved method and apparatus for use in detecting the presence of particles on a surface using the light scattering principle.

It is another object of this invention to provide a method and apparatus as described above in which the surface being examined is illuminated from all directions with a beam of light incident on the surface at an oblique angle and forming a small spot on the surface.

It is still another object of this invention to provide a novel optical arrangement for illuminating a spot on a surface with light from all directions and then detecting light scattered from any particles on the surface.

It is yet still another object of this invention to provide a method and apparatus as described above which utilizes mirrors which are only first surface reflecting.

It is a further object of this invention to provide a method and apparatus as described above in which the scattered light is imaged through a continuous tube onto a light detector.

It is another object of this invention to provide a method and apparatus as described above wherein unwanted scattered light is reduced to a minimum.

It is still another object of this invention to provide a method and apparatus as described above in which a sample being tested is illuminated an area at a time.

It is another object of this invention to provide a system for examining surfaces useful in applications requiring illumination by an ultraviolet light beam.

It is a further object of this invention to provide a system designed especially for use in dark field illumination applications.

The foregoing and other objects and advantages will appear from the description to follow. In the description, reference is made to the accompanying drawing which forms a part thereof, and in which is shown by way of illustration, a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is, therefore, not to taken in a limiting sense, and the scope of the present invention is best defined by the appended claims.

SUMMARY OF THE INVENTION

Apparatus for use in detecting particles on a surface of an object constructed according to the teachings of the present invention comprises a holder for holding said object, means for generating a collimated beam of light, first front surface reflecting mirror means for deflecting said collimated beam outward in all directions and converting said collimated beam into a converging beam, second front surface reflecting mirror means for directing said light reflected by said first mirror means inward toward said surface from all directions at a small angle whereat said light will strike said surface and come to focus thereon as a spot, a light detector, lens means for collecting light scattered by any particles on said surface illuminated by said light and imaging said light collected on said light detector, and means for moving said holder relative to said impinging light beam so that the entire surface of said object can be illuminated a spot at a time.

A method for use in detecting particles on a surface of an object according to the teachings of the present invention comprises generating a collimated beam of light, directing said collimated beam of light toward said surface from all directions at an oblique angle thereto and bringing said collimated beam to focus on said surface, focussing an electro-optical light detector on said surface in a position so as to detect scattered light only said scattered light indicating the presence of particles, moving said surface relative to said impinging light beam so as to enable said impinging light to scan the entire area of said surface.

BRIEF DESCRIPTION OF THE DRAWINGS

In the drawings wherein like reference numerals represent like parts.

DETAILED DESCRIPTION OF PREFERRED EMBODIMENTS

Figure 1:
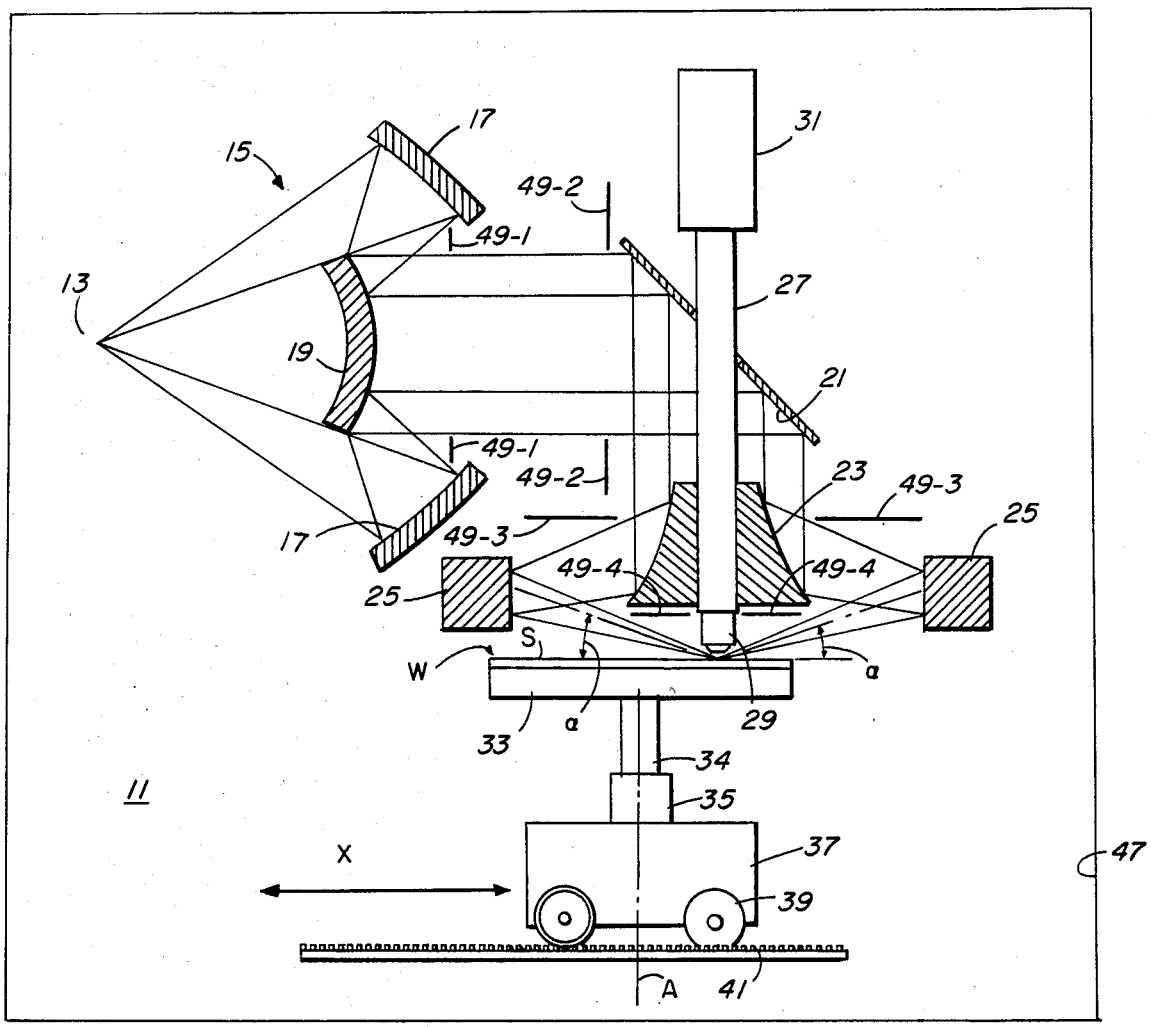
FIG. 1 is a diagram of an embodiment of a system constructed according to the teachings of the present invention.

Referring now to the drawings there is illustrated in FIG. 1 an apparatus for use in detecting the presence of particles on the surface of an object W and identified generally by reference numeral 11. Object W may be for example, a semiconductor wafer.

Apparatus 11 includes a light source 13, such as a mercury arc lamp, for generating a beam of light. The beam of light produced by light source 13 is collimated by a Cassegrain collimator 15 to produce a collimated beam of light. The Cassegrain collimator includes a primary mirror 17 and a second mirror 19. Because of the construction of the Cassegrain collimator 15, and in particular, the location of secondary mirror 19 relative to primary mirror 17, the collimated beam produced is annular in cross section rather than circular in cross section.

The collimated beam of light from Cassegrain collimator 15 impinges on a 45° annular shaped planar mirror 21. Light reflected by mirror 21 impinges on an annular shaped inverted parabolic mirror 23. As can be seen, mirror 23 is essentially an annular shaped frustoconical element in which the (outer) reflective surface 23-1 is a parabolic segment rather than flat. Mirror 23 performs two functions, namely, (1) causes the collimated beam impinging thereon to be reflected outward in all directions and slightly downward and (2) causes the collimated beam incident thereon to be made converging.

The converging light beam from mirror 23 impinges on the inside surface 25-1 of a ring mirror 25. Light impinging on ring mirror 25 is reflected inward and downward toward the surface S of the object W being examined at a very small angle to the surface S, such as an angle between about 4° and 12° and is brought to focus on surface S as a small spot. As can be appreciated, the small spot formed on the surface S is essentially an image of light source 13.

Figure 4:
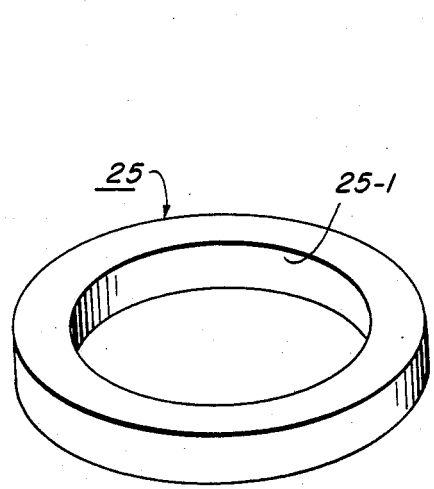
FIG. 4 is a perspective view of the ring mirror shown in FIG. 1.
Figure 2:
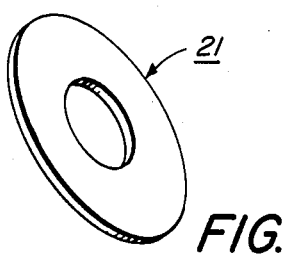
FIG. 2 is a perspective view of the 45° mirror shown in FIG. 1.
Figure 3:
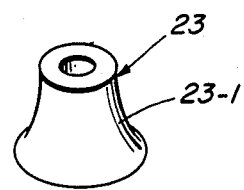
FIG. 3 is a perspective view of the parabolic mirror shown in FIG. 1.

Perspective views of mirrors 21, 23 and 25 are shown in FIGS. 2, 3 and 4 respectively.

Light impinging on surface S is reflected by surface S at an angle of reflection equal to the angle of incidence. On the other hand, any particle or particles present on the surface (over the area illuminated) will scatter the impinging light in all directions, including vertically upward.

An elongated continuous (i.e. having no openings along its length) light tight tube 27 having an outside diameter less than center (blind spot) of the collimated beam from the Cassegrain collimator is positioned a distance vertically above the surface S at the spot where surface S is illuminated by the incident light. An objective lens 29 is fixedly mounted on the lower end of tube 27 and a light detector 31, such as a photomultipler tube is fixedly mounted on the upper end of tube 27. Tube 27 is in axial alignment with the optical axes of mirrors 21, 23 and 25.

Light scattered upward from surface S, but not light reflected by surface S, is collected by objective lens 29 and imaged on the light sensitive surface of light detector 31.

Sample S is mounted on a holder 33 and maintained thereon by any suitable means (not shown) such as suction. Holder 33 is mounted on a vertical shaft 34 which is rotatable about its longitudinal axis A by means of a motor 35 so as to provide rotational movement of object W relative to the incident light. Motor 35 is mounted on a carriage 37 which is mounted by wheels 39 on rails 41 for movement back and forth in the "X" direction by any suitable means, such as a motor inside the carriage 37 (not shown) to provide translational movement of object W relative to the impinging light. Thus, the entire surface area of object W can be scanned, a spot at a time, buy the impinging spot of light.

Finally, apparatus 11 includes a light tight housing 47 having a reflectionless interior surface and a set of four baffles 49-1, 49-2, 49-3 and 49-4 to insure that only light scattered by the impinging spot will be collected by the object lens.

The output of light detector 29 may be stored and/or processed and/or displayed as desired by any suitable means such as a computer (not shown).

One important advantage of the invention is that only a very small spot (equal to the size of the light source) on the surface is illuminated at one time rather than the entire surface. Thus, a very small area on the surface receives all available light at almost grazing incidence and can be examined under high intensity illumination. Also, by varying the size of the object lens 29, the amount by which the image is magnified on the surface of light detector 31 can be changed as desired.

As is readily apparent, the light beam from source 11 does not pass through any optical elements but rather is reflected off the front surfaces of the various mirrors 21, 23 and 25. Thus, the possibility of any unwanted scattered light that may be caused by the light beam passing through glass and the like is completely eliminated. It is also to be noted that although the beam of light emitted by the Cassegrain collimator is annularly shaped the beam of light striking the 45° mirror will not be completely annularly shaped but rather will have a dark area corresponding to where the beam strikes tube 27.

Instead of having a Cassegrain collimator in front of the light source 13 to produce an annular shaped light beam, a front surface spherical or parabolic mirror that produces a collimated light beam located behind the light source and a mask in front of the light source could be employed. Parabolic mirrors are preferred to spherical mirrors since they will produce a sharper image of the source. Light source 13 may be any source which when focused (imaged) on surface S will provide a very small spot. An example of another such light source is a xenon arc lamp or a light brought to focus at a pinhole. Also, the annular shaped collimated beam could be produced by a laser followed by a beam expander and a mask. Instead of a photomultiplier tube, light detector 31 may be a photodiode array or a vidicon. If a vidicon is used the entire area of the spot illuminated is scanned a point at a time by the electron beam gun in the vidicon tube. Instead of achieving relative translational movement of the incident light beam relative to the surface S by moving holder 33 back and forth, carriage 35 could be stationary and the relative movement achieved by mounting mirrors 21 and 23 and 25 and tube 27 on a frame that is movable back and forth from the Cassegrain collimator 15 along an axis parallel to the emerging collimated beam.

The embodiment of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. Apparatus for use in detecting particles on the surface of an object comprising:
    a. a holder for holding said object,
    b. means for generating a collimated beam of light annularly shaped in cross section,
    c. first curved front surface reflecting mirror means disposed along the optical axis of said collimated beam for deflecting said collimated beam outward in all directions and converting said collimated beam into a converging beam,
    d. second curved front surface reflecting mirror means disposed along the optical axis of said collimated beam in axial alignment with said first front surface reflecting mirror means for directing said light reflected by said first mirror means inward toward said surface from all directions at a small angle whereat said light will strike said surface and come to focus thereon as a spot,
    e. a light detector,
    f. lens means in axial alignment with said first and second front surface reflecting mirror means for collecting light scattered by any particles on said surface illuminated by said light and imaging said light collected on said light detector, and
    g. means for moving said holder relative to said impinging light beam so that the entire surface of said object can be illuminated a spot at a time.

2. Apparatus for use in detecting particles on the surface of an object comprising:
    a. a holder for holding said object,
    b. means for generating a collimated beam of light annularly shaped in cross-section,
    c. first front surface reflecting mirror means comprising an annular shaped inverted parabolic mirror for deflecting said collimated beam outward in all directions and converting said collimated beam into a converging beam,
    d. second front surface reflecting mirror means comprising a ring mirror for directing said light reflected by said first mirror means inward toward said surface from all directions at a small angle whereat said light will strike said surface and come to focus thereon as a spot,
    e. a light detector,
    f. lens means for collecting light scattered by any particles on said surface illuminated by said light and imaging said light collected on said light detector, and
    g. means for moving said holder relative to said impinging light beam so that the entire surface of said object can be illuminated, a spot at a time.

3. The apparatus of claim 2 and further including a light tight tube having a first end and a second end and wherein said lens means is mounted at said first end of said tube and said light detector is mounted at said second end of said tube.

4. The apparatus of claim 2 and further including a 45° mirror disposed between said means for generating said collimated beam of light and said first mirror means for reflecting said collimated beam in the direction of said first mirror means.

5. The apparatus of claim 4 and wherein said 45° mirror is annularly shaped.

6. The apparatus of claim 4 and wherein said electrooptical light detecting means is a photomultiplier tube.

7. The apparatus of claim 4 and wherein said electrooptical light detecting means is a vidicon.

8. The apparatus of claim 4 and wherein said electrooptical light detecting means is a photodiode array.

9. The apparatus of claim 4 and wherein said means for generating a collimated beam of light having an annular shaped cross section comprises a light source for generating a beam of light and a Cassegrain collimator.

10. The apparatus of claim 4 and wherein said means for generating a collimated beam of light having an annular shaped cross section comprises a light source, a collimating mirror and a mask.

11. The apparatus of claim 9 and wherein the light source is a mercury arc lamp.

12. The apparatus of claim 4 and wherein said lens means mounted on said tube comprises an objective lens.

13. The apparatus of claim 2 and wherein said light beam impinges on said surface at an angle of between around 78° to 86° from normal incidence.

14. The apparatus of claim 2 and wherein said holder for holding said object comprises a platform.

15. The apparatus of claim 2 and wherein said means for moving said holder relative to said light beam comprises a motor for rotating said platform about a vertical axis.

16. The apparatus of claim 2 and wherein said means for moving said holder relative to said light beam comprises means for moving said holder back and forth in a horizontal plane relative to said impinging light.

17. The apparatus of claim 2 and further including a light tight housing having a light reflectionless interior.

18. A method of detecting particles on a surface of an object comprising:
   a. generating a collimated beam of light annularly shaped in cross-section,
   b. directing said collimated beam of light toward said surface from all directions at an oblique angle thereto and bringing said collimated beam to focus on said surface through an inverted annular shaped parabolic mirror and a ring mirror,
   c. focussing an electro-optical light detector on said surface in a position so as to detect scattered light only, said scattered light indicating the presence of particles,
   d. moving said surface relative to said impinging light beam so as to enable said impinging light to scan the entire area of said surface.

* * * * *